(12) United States Patent
Kolobow

(10) Patent No.: US 6,655,382 B1
(45) Date of Patent: Dec. 2, 2003

(54) SPONTANEOUS BREATHING APPARATUS AND METHOD

(75) Inventor: Theodor Kolobow, Rockville, MD (US)

(73) Assignee: The United States of America as represented by the Secretary of Health and Human Services, Washington, DC (US)

(*) Notice: Subject to any disclaimer, the term of this patent is extended or adjusted under 35 U.S.C. 154(b) by 0 days.

(21) Appl. No.: 09/555,229
(22) PCT Filed: Sep. 18, 1997
(86) PCT No.: PCT/US98/19714
§ 371 (c)(1), (2), (4) Date: May 26, 2000
(87) PCT Pub. No.: WO99/13933
PCT Pub. Date: Mar. 25, 1999

Related U.S. Application Data

(63) Continuation of application No. 08/933,003, filed on Sep. 18, 1997, now abandoned.
(60) Provisional application No. 60/059,251, filed on Sep. 18, 1997.

(51) Int. Cl.[7] .................................................. A62B 9/00
(52) U.S. Cl. .......................... 128/204.25; 128/205.24; 128/207.14; 128/207.16
(58) Field of Search ................ 128/200.14, 200.24, 128/201.28, 203.12, 204.18, 204.21, 204.25, 204.26, 205.11, 205.24, 207.14, 207.16

(56) References Cited

U.S. PATENT DOCUMENTS

| | | |
|---|---|---|
| 3,815,606 A | 6/1974 | Mazal |
| 4,082,093 A | 4/1978 | Fry et al. |
| 4,872,579 A | 10/1989 | Palmer .................. 128/205.19 |
| 4,924,862 A | 5/1990 | Levinson ................ 128/207.16 |
| 5,186,167 A | 2/1993 | Kolobow ................ 128/207.14 |
| 5,513,628 A | 5/1996 | Coles et al. ........... 128/200.26 |
| 5,544,648 A | 8/1996 | Fischer, Jr. |
| 5,785,050 A | 7/1998 | Davidson et al. ...... 128/205.24 |
| 5,878,743 A | 3/1999 | Zdrojkowski et al. . 128/204.23 |

FOREIGN PATENT DOCUMENTS

DE 4221931 C1 7/1993

Primary Examiner—Glenn K. Dawson
(74) Attorney, Agent, or Firm—Venable LLP; Chad C. Anderson

(57) ABSTRACT

A spontaneous breathing apparatus and method. The apparatus includes: a source of oxygen containing gas (7); a catheter (5) in flow communication with the source of oxygen containing gas (7) and configured to be introduced into a subject's trachea (1) through a tracheostomy for delivering oxygen containing gas therein; a tracheostomy tube (9) disposed adjacent the catheter (5) and having one end configured to be disposed in the subject's trachea (1); and a pressure actuated threshold valve (32) connected to another end of the tracheostomy tube (9), the valve (32) being configured for venting a gas existing within the subject's trachea (1) at the one end of the tracheostomy tube (9) when the gas exceeds a threshold pressure of the valve (32), the valve (32) thereby being effective for reducing pressure within the subject's trachea 1) when the pressure within the subject's trachea (1) exceeds the threshold pressure.

8 Claims, 4 Drawing Sheets

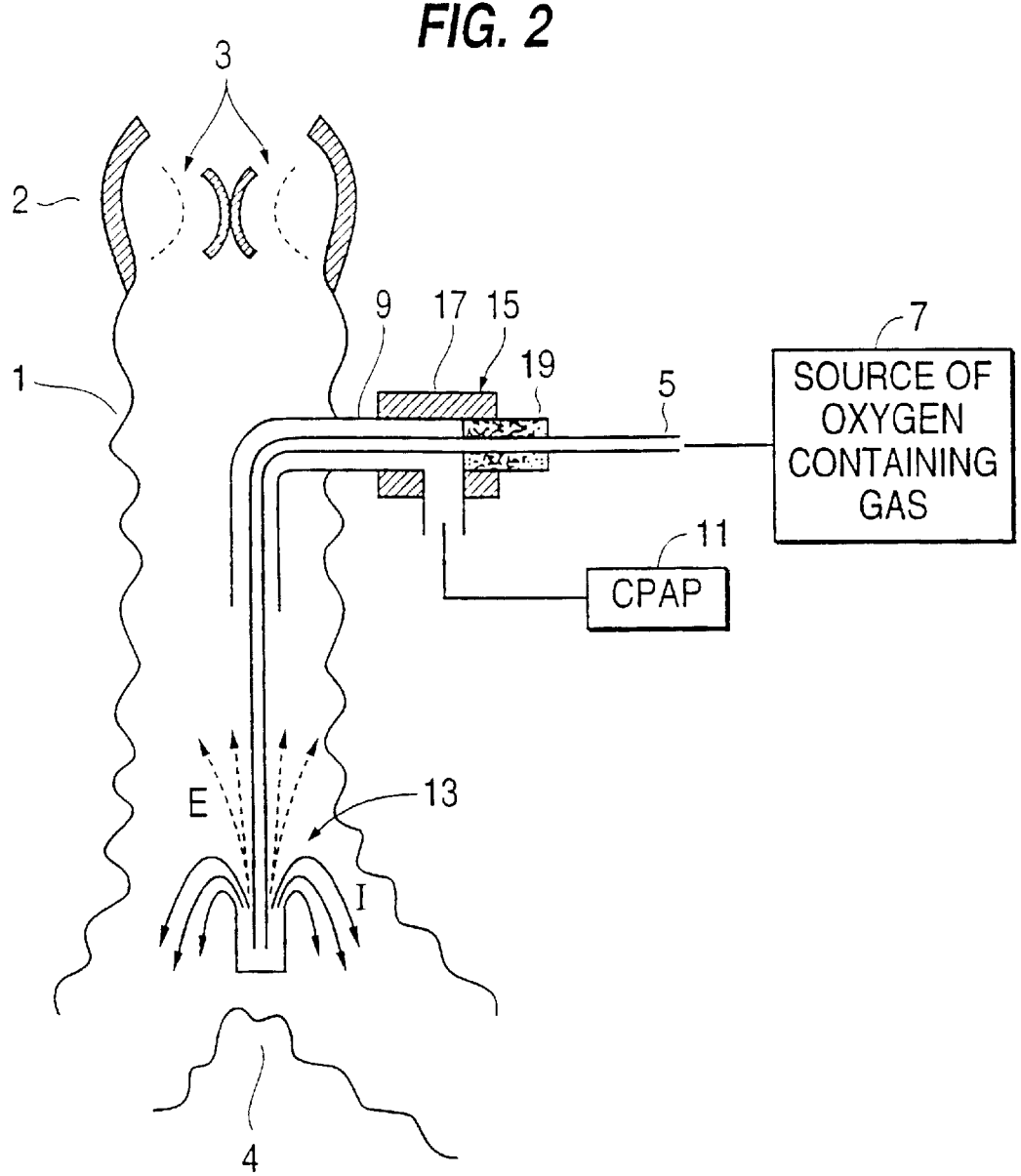

SPONTANEOUS BREATHING APPARATUS AND METHOD

This application is a continuation of Ser. No. 08/933,003 filed Sep. 18, 1997, now abandoned, which claims the benefit of provisional application No. 60/059,251 filed on Sep. 18, 1997.

FIELD OF THE INVENTION

The invention relates to breathing apparatuses and methods.

BACKGROUND OF THE INVENTION

Tracheal gas insufflation (TGI) used in breathing apparatuses combined with mechanical ventilation (MV) through an endotracheal tube results in reduced dead space ventilation, and allows use of lower respiratory rates and tidal volumes at lower peak inspiratory pressures (PIP). In its simplest form, in TGI, a straight catheter with an open tip or side holes delivers a supply of fresh oxygen containing gas to flush out the anatomical dead space. Dead space is determined from the volume of the trachea and tracheostomy or endotracheal tube utilized, which, for example, can be about 120 cc in an adult. The catheter may be introduced into a patient's trachea either through an endotracheal tube, or percutaneously through a tracheostomy.

One example of a prior art breathing apparatus is provided in U.S. Pat. No. 5,186,167 (hereinafter "U.S. Pat. No. 5,186,167"), which discloses a method and apparatus for intratracheal ventilation (ITV) and intratracheal pulmonary ventilation (ITPV) in which a reverse thrust catheter (RTC) positioned in a patient's trachea at the carina supplies a constant supply of fresh oxygen containing gas to flush anatomical dead space. The catheter includes a catheter tip which directs the constant supply of fresh oxygen containing gas in a manner so as to create sub-atmospheric pressures near the carina and thus allows control of intratracheal airway pressures during the entire respiratory cycle and prevents overinflation of the lungs. The distal end of the catheter preferably includes a diffuser which is positioned at a level near the patient's carina, and which includes a plurality of gas passage ports along the length thereof. At high gas flow rates through the catheter, which may be ideal for a particular treatment protocol, the pressure created by a stream of fresh air and oxygen may result in some back pressure, which can impair expiration and keep the lungs continuously overinflated. To overcome the problem of back pressure, and to provide a way of controlling intratracheal airway pressures during the entire respiratory cycle, the tip of the catheter is provided with the diffuser, which serves to distribute the fresh air and oxygen into the trachea while eliminating the distal jet effect provided by an open ended catheter. By avoiding the distal jet effect, the use of the diffuser has been found to significantly reduce the distal airway pressures. U.S. Pat. No. 5,186,167 proposes using a tubular portion with a closed distal end at the catheter tip and with an annular opening or gas exit port to provide a controlled low pressure zone near the carina. The gap "a" of the annular opening or exit port determines the flow-pressure characteristics at the level of the carina for any given gas flow rate, and is disclosed as being small, that is, in the range from 0.005 to 0.020 inch. The disclosure in U.S. Pat. No. 5,186,167 is incorporated herein by reference.

U.S. Pat. No. 5,544,648 pertains to a device for creating a sub-atmospheric pressure near the carina of a subject which includes a channel or perforation for the passage of an oxygen-containing gas therethrough. The channel or perforation is open in a direction distal of the subject so as to establish a zone of sub-atmospheric pressure by reverse venturi effect during patient exhalation. The sub-atmospheric pressure in the zone facilitates removal of carbon dioxide from the lungs of the patient and permits intratracheal and/or intratracheal pulmonary ventilation to be performed at pressures less than those conventionally required for such ventilation. The above device is generally of the type described in U.S. Pat. No. 5,186,167 (i.e.: a RTC). According to U.S. Pat. No. 5,544,648, the device obviates the risks inherent in RTC's, specifically, the possibility of detachment of a tubular member in those devices, and the possible complications of surgical recovery of the tubular member from the bronchi or lungs of the subject. The device in U.S. Pat. No. 5,544,648 achieves the above by either eliminating the tubular member of prior reverse venturi devices, or by providing a shoulder affirmatively preventing distal movement and loss of it.

In pilot studies in sheep using breathing apparatuses of the prior art, it has been found that the early response after a RTC, such as the one described in U.S. Pat. No. 5,186,167, was introduced percutaneously through a mini-tracheostomy into the trachea of non-intubated awake sheep was similar to what has been observed in intubated sheep (where the catheter is introduced into the trachea of the sheep through an endotracheal tube), namely, a decrease in respiratory rate, lower spontaneous tidal volume and decreased effort of breathing. However, after some minutes to hours, the breathing pattern of the sheep was observed to change, vacillating between a normal pattern and a new, unexpected pattern. In this unexpected pattern, upon spontaneous prolonged closing of the glottis of the sheep (i.e. the voice box of an animal, containing the vocal folds, together with accessory muscles used in phonation), the insufflated gas accumulated within the lungs, passively expanded the same without effort on the part of the sheep. This expansion of the lungs was observed to be eventually relieved by a spontaneous opening of the glottis, leading to expiration. The above unexpected pattern was observed to be marked by measured intrapulmonary airway pressures which were frequently dangerously high.

In this respect, it is noted that the glottis of the sheep is active both during inspiration and expiration, and acts as a valve which opens and closes the trachea and hence the lungs to the surrounding atmosphere. Closing of the glottis prevents loss of air through the mouth and the nose, resulting in inspiration brought about by the introduction of oxygen containing gas into the trachea through the catheter. Given that the total work needed to activate a muscle innervating the glottis (which weighs less than 1 g) is negligible, and given that little or no effort is needed to expand the chest wall or to move the diaphragm, in essence, the potential energy from the compressed gas being introduced into the trachea through the catheter was spent in the above experiment to expand the lungs, expiration remaining passive. However, disadvantageously, as previously described, the expansion of the lungs led to dangerously high pressures existing frequently therein during the respiratory cycle, which pressures were not effectively relieved by a spontaneous opening of the glottis.

SUMMARY OF THE INVENTION

It is an object of the invention to overcome the disadvantages associated with the prior art by providing a spontaneous breathing apparatus and method which eliminate the build up of dangerously high pressures in the lungs of a subject during insufflation.

It is another object of the invention to provide a spontaneous breathing apparatus and method which obviate the use of an endotracheal tube, thus eliminating the need for cleaning the tube intermittently. Cleaning the endotracheal tube commonly involves suctioning through external means. The above procedure is not only uncomfortable and cumbersome to the subject, but also increases the risk of introducing bacterial infections, such as nosocomial pneumonia, into the trachea by virtue of the frequent manipulation of the breathing apparatus associated with the endotracheal tube. The spontaneous breathing apparatus according to the invention eliminates the above disadvantages, providing spontaneous, on-line cleaning of mucus from the trachea. Additionally, the elimination of an endotracheal tube from the spontaneous breathing apparatus advantageously decreases the risk of tracheal aspiration, and further does not interfere with swallowing, eating, drinking, speech and cough.

It is a further object of the invention to provide a spontaneous breathing apparatus which includes a catheter configured for promoting mucous flow in a direction outside of the trachea, thus aiding mucociliary transport. This embodiment is capable of controlling intratracheal airway pressures during the respiratory cycle while substantially reducing the risk of tracheal injury from the jet of air emanating from the catheter.

The above objects, together with other objects to become apparent as the description progresses, are accomplished according to the invention by the provision of a spontaneous breathing apparatus comprising: a source of oxygen containing gas; a catheter in flow communication with the source of oxygen containing gas and adapted to be introduced into a subject's trachea through a tracheostomy for delivering oxygen containing gas therein; a tracheostomy tube disposed adjacent the catheter and having one end adapted to be disposed in the subject's trachea; and a pressure actuated threshold valve being connected to another end of the tracheostomy tube, the valve being configured for venting a gas existing within the subject's trachea at the one end of the tracheostomy tube when the gas exceeds a threshold pressure of the valve, the valve thereby being effective for reducing pressure within the subject's trachea when the pressure within the subject's trachea exceeds the threshold pressure.

According to another aspect of the invention, the catheter is a reverse thrust catheter comprising a venturi end adapted to direct a flow of the oxygen containing gas in a direction substantially toward the subject's glottis.

According to yet another aspect of the invention, the venturi end comprises: a catheter tip defining a plurality of holes therein for allowing the oxygen containing gas to exit from the catheter; and a tubular portion connected to the catheter tip for directing the oxygen containing gas emerging from the holes in the direction substantially toward the subject's glottis, the tubular portion and an outer circumference of the catheter together defining a venturi gap therebetween.

According to a further aspect of the invention, the venturi gap is approximately 0.025 inch.

According to one aspect of the invention, the catheter is disposed substantially within the tracheostomy tube thereby forming a catheter-tube assembly, the catheter-tube assembly being adapted to be inserted into the subject's trachea through a single tracheostomy.

According to a further aspect of the invention, the pressure actuated threshold valve is a continuous positive airway pressure valve (continuous positive airway pressure valve).

According the yet another aspect of the invention, the pressure actuated threshold valve includes a sensor therein for sensing an actuation of the valve to release the gas within the subject's trachea when the pressure within the subject's trachea exceeds the threshold pressure, the apparatus further comprising an actuator for stopping, or reducing, a flow of the oxygen containing gas from the source of oxygen containing gas into the catheter when the sensor senses an actuation of the valve.

The objects of the invention are further achieved by a method comprising the steps of: providing a source of oxygen containing gas; placing a catheter in flow communication with the source of oxygen containing gas; introducing the catheter into a subject's trachea through a tracheostomy for delivering oxygen containing gas therein; providing a tracheostomy tube disposed adjacent the catheter; placing one end of the tracheostomy tube in the subject's trachea; connecting a pressure actuated threshold valve having a gas vent to another end of the tracheostomy tube; and venting, through the valve, a gas existing within the subject's trachea at the one end of the tracheostomy tube when the gas exceeds a threshold pressure of the valve thereby limiting pressure within the subject's trachea when the pressure within the subject's trachea exceeds the threshold pressure.

According to one aspect of the invention, the tracheostomy tube includes a cuff at the one end thereof, the method involving the step of preventing the cuff from inflating during a respiratory cycle of the subject.

A threshold CPAP valve is an important part of the invention, as the apparatus according to the invention mimics a spontaneous form of Airway Pressure Release Ventilation, although its mechanism is different.

The present invention pertains to an apparatus and method suitable for patients with acute or chronic respiratory failure that dispenses with oro-nasotracheal intubation, greatly decreases anatomic dead space ventilation, leads to spontaneous ventilation at small tidal volumes and at low respiratory rates, eliminates the need for tracheal suctioning (cleaning) and greatly decreases the effort of spontaneous breathing, further greatly reducing the need for mechanical ventilation.

The apparatus and method according to the invention are simple and relatively noninvasive, and allow spontaneous breathing in a model of severe acute respiratory failure, without intubation and without adverse effects therefrom, without the need to use a mechanical ventilator, creating a controllable mean airway pressure, facilitating tracheal self cleaning via the RTC, and permitting coughing, eating, drinking and vocalization.

BRIEF DESCRIPTION OF THE DRAWINGS

The foregoing objects of the invention, together with other objects and advantages which may be attained by its use, will become more apparent upon reading the following detailed description of the invention taken in conjunction with the drawings. In the drawings, where like reference numerals identify corresponding components:

FIG. 2 is a schematic cross-sectional view of a trachea penetrated by a RTC and a TT in a second embodiment of a spontaneous breathing apparatus according to the invention;

FIG. 3b is a schematic, side elevational, enlarged view of the venturi tip of the RTC shown in FIG. 3a.

DETAILED DESCRIPTION OF THE INVENTION

Figure 1:
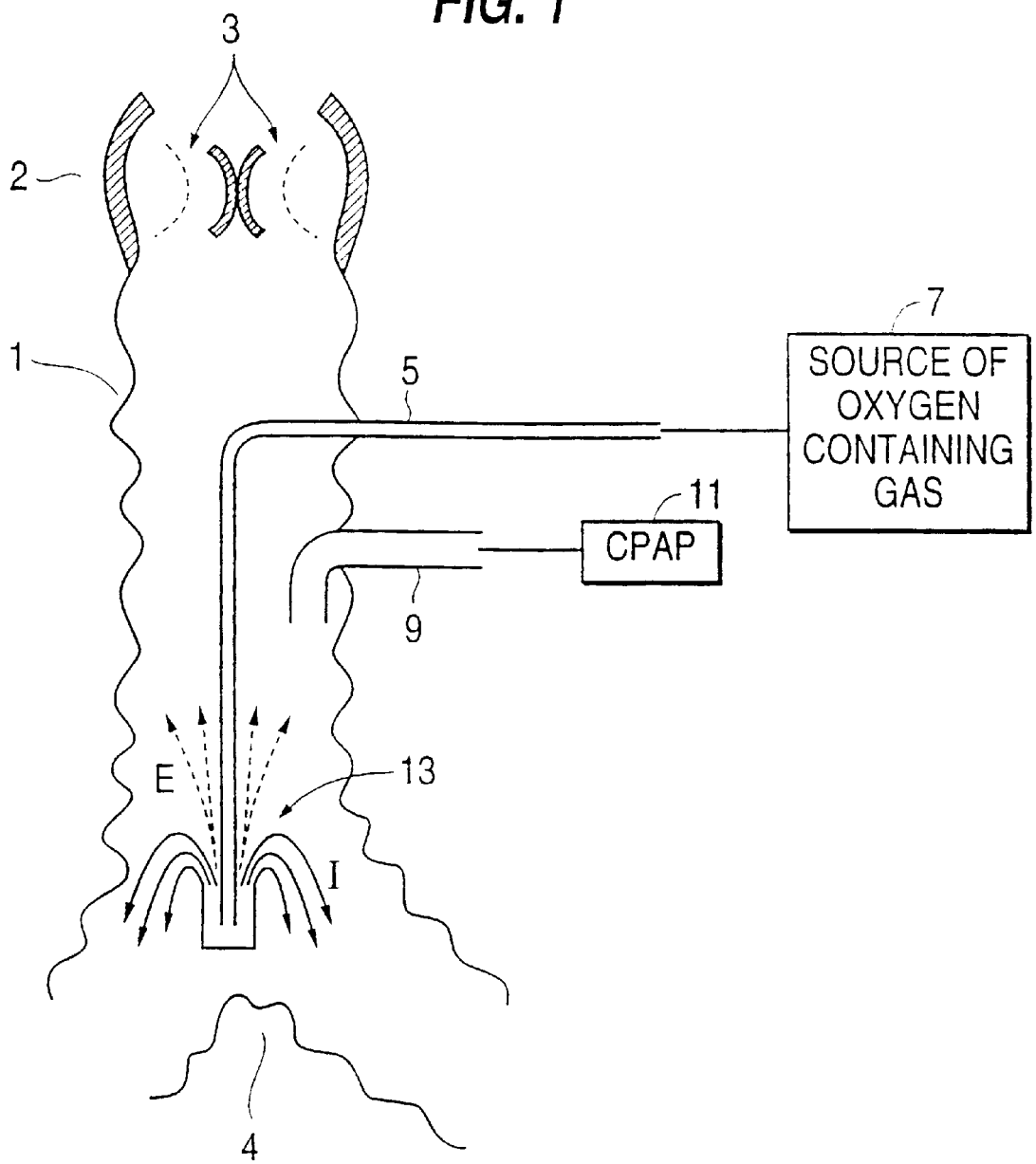
FIG. 1 is a schematic cross-sectional view of a trachea penetrated by a RTC and a tracheostomy tube (TT) in a first embodiment of a spontaneous breathing apparatus according to the invention.

Referring now to FIGS. 1 and 2, a trachea 1 is shown in schematic form, including vocal folds 3 in the region of the larynx or glottis. Vocal folds 3 are shown in these figures in broken lines to suggest an open position, and in solid lines to suggest a closed position. Trachea 1 is penetrated by a RTC catheter 5, which is in flow communication with a source of oxygen containing gas 7 for delivering the gas to the carina 4 of the subject. Source 7 may be any conventional source of oxygen containing gas used in breathing apparatuses.

In FIG. 1, the trachea is additionally penetrated by a thin walled TT 9 connected to a threshold CPAP valve 11. In FIG. 2, the RTC is held within the TT at its region of penetration into the trachea, the apparatus of FIG. 2 thus necessitating a single mini-tracheostomy. Threshold CPAP valve 11 may be any conventional valve which is actuated to release the gas within TT 9 as a function of the pressure existing within the TT. The tip of RTC 5 is provided with a reverse venturi end 13 shown schematically in FIGS. 1 and 2, and described in further detail below in relation to FIGS. 3a and 3b. As seen in FIGS. 1 and 2, during inspiration when vocal folds 3 are closed as suggested in solid lines, the oxygen containing gas carried into the carina is released in the direction of the vocal folds and, because of lower pressures in the bronchi, is diverted into the bronchi as suggested by solid arrows I. During expiration when vocal folds 3 are open, as suggested in broken lines, the oxygen containing gas, if it is still being supplied through the RTC, is released together with the carbon dioxide containing gas exiting the lungs in the direction of the vocal folds, and continues in this direction until it exits the trachea, as suggested by broken arrows E. According to the invention, gases in the lungs may be released either through the vocal folds 3 if the folds are open, or through the threshold CPAP valve 11, as will be described in further detail below.

In FIG. 2, RTC 5 is held within TT 9 as described above, and is positioned therein outside the trachea by a holding device 15 as shown. Holding device 15 is configured to direct RTC 5 in the direction of the source of oxygen containing air 7 on the one hand, and further to allow TT 9 to be placed in flow communication with threshold CPAP valve 11. For example, as shown in FIG. 2, holding device 15 may include an outer shell which accommodates the outer end of TT 9 therein, and an end plug 19 received matingly within one end of outer shell 17 and accommodating RTC 5 therein for centering the RTC inside the TT in a region outside of the tracheostomy.

Figure 3A:
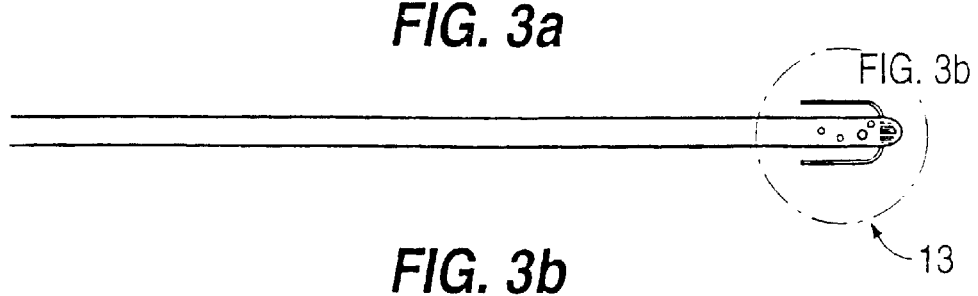
FIG. 3a is a schematic, side elevational view of a venturi end of a RTC of the spontaneous breathing apparatus according to the invention.
Figure 3B:
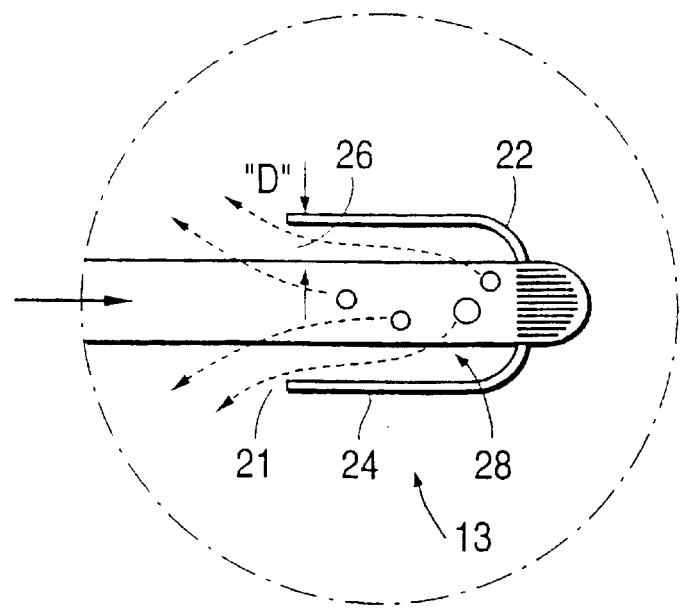

As seen in FIGS. 3a and 3b, reverse venturi end 13 at the tip of RTC 5 is designed to direct the flow of air and oxygen exiting from the end of the RTC away from carina 4. Accordingly, venturi end 13 includes a gas exit port 21 which directs the flow of air and oxygen away from the distal end 22 of the catheter tip. In a preferred embodiment, the catheter tip includes a tubular portion 24 having a closed distal end 22 which is fixed to the end of RTC 5. The tubular portion 24 further has an opened end 26 which defines an annular opening or gas exit port 21. The end of the catheter which is enclosed by the tubular portion of the catheter tip includes a number of openings 28 through which air and oxygen pass from catheter 5 through the exit port 21. The gap "D" of the annular opening 21 determines the flow pressure characteristics at the level of the carina for any given gas flow rate. The gap "D" is selected according to the present invention to be approximately 0.025 inch.

Figure 4:
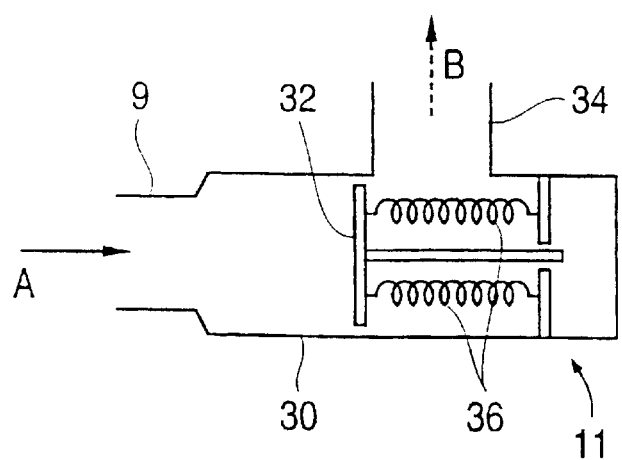
FIG. 4 is a schematic view of a threshold CPAP valve used in the spontaneous breathing apparatus of the invention.

As seen in FIG. 4, a conventional CPAP valve is shown in schematic form. Threshold CPAP valve 11 includes a body 30 including a spring-actuated disc valve 32 therein. Disc valve 32 is in pressure communication with TT 9 as shown. Body 30 of CPAP valve 11 further defines a gas vent 34. In operation, when the pressure inside TT 9, as depicted schematically by arrow A, exceeds a threshold pressure as determined by the springs 36, disc valve 32 is moved in a direction to allow gases within TT 9 to be vented through gas vent 34, as depicted by broken arrow B. Thus, it is clear that selection of threshold CPAP valve 11 determines the threshold pressure within TT 9, and hence within the lungs.

Figure 5:
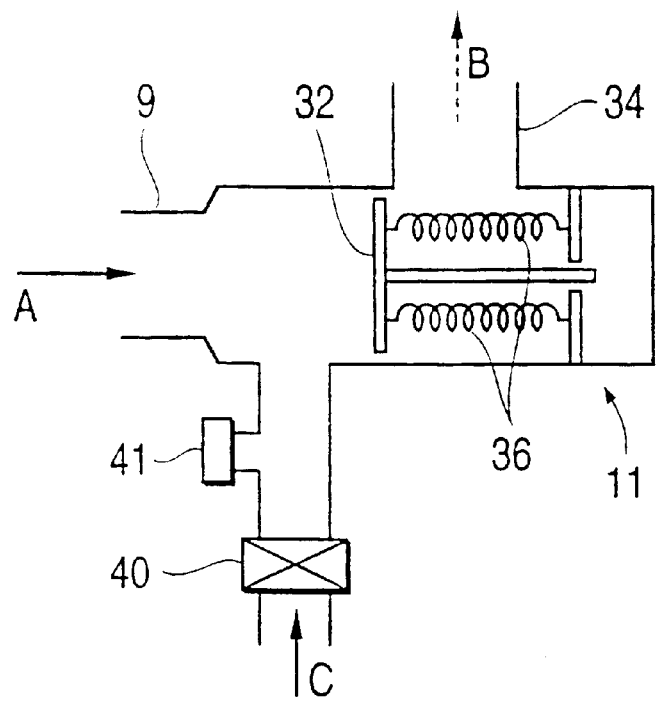
FIG. 5 is a schematic view of another embodiment of the threshold CPAP valve of FIG. 4 used in the spontaneous breathing apparatus of the invention.

FIG. 5 depicts a schematic view of another embodiment of the threshold CPAP valve of FIG. 4. In FIG. 5, additional air and/or oxygen can be delivered through valve 40 in the direction of arrow C during any phase of the inflation cycle, as determined by pressure sensor 41. The additional air and/or oxygen can be delivered when gas flow through the RTC catheter is flow limited, or when a more rapid raise in airway pressure is desired.

Figure 6:
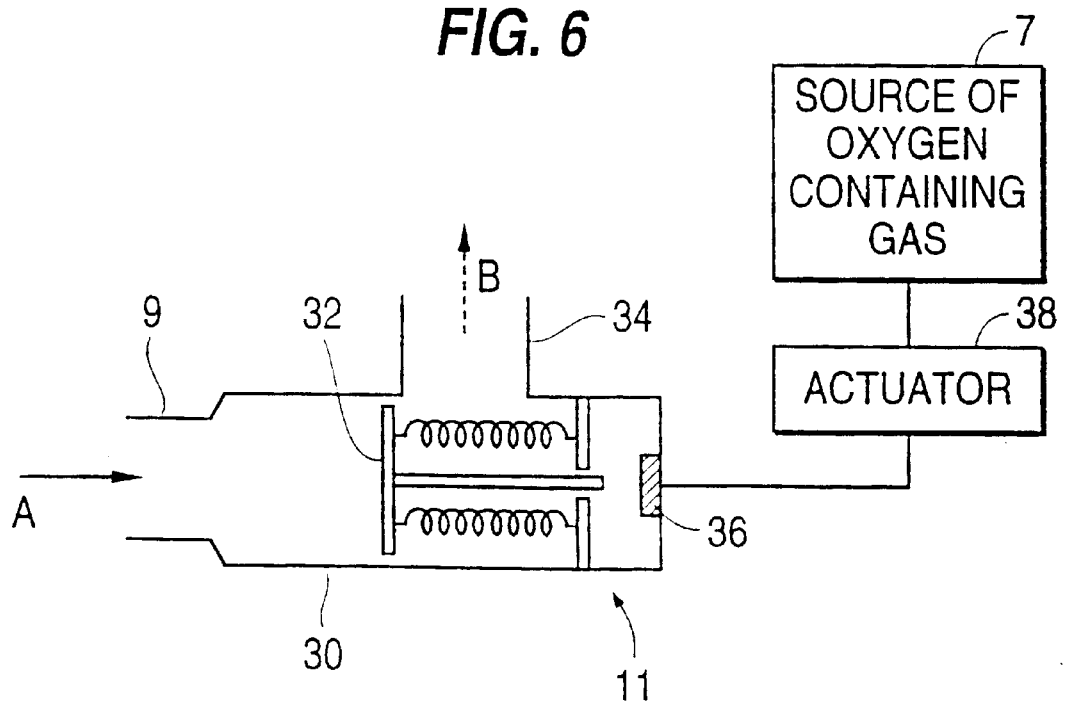
FIG. 6 is a schematic view of the threshold CPAP valve of FIG. 4 coupled to a source of oxygen containing gas used in the spontaneous breathing apparatus of the present invention.

As shown in FIG. 6, the threshold CPAP valve 11 shown in FIG. 4 may be modified to include a sensor 36 for sensing an actuation of valve 11 in response to a threshold pressure within TT 9. As shown in the figure, this sensor is coupled to an actuator 38 which, in a conventional manner, shuts off, or decreases, the source of oxygen containing air with respect to RTC 5, thus causing source 7 to stop or decrease the delivery of oxygen containing gas to the catheter. In the above arrangement, when the threshold pressure is exceeded in the region of the carina as sensed by threshold CPAP valve 11, the gases within the lungs are vented through gas vent 34, while, at the same time, the supply of oxygen containing gas to RTC 5 is stopped or decreased.

In operation, oxygen containing gas is delivered into the trachea through the RTC either continuously, or intermittently if the spontaneous breathing apparatus contains a valve as shown in FIG. 6. During inspiration, the oxygen containing gas enters the lungs, as shown by solid arrows I in FIGS. 1 and 2, the vocal folds closing spontaneously. During expiration, the vocal folds open spontaneously, letting gases exit the lungs, in which case the oxygen containing gas exits the venturi end 13 of RTC 5 as shown by broken arrows E in FIGS. 1 and 2. In the event the vocal folds remain closed during the time period when expiration is to occur, pressure builds up in the lungs and trachea. When this pressure reaches a threshold value as determined by the threshold CPAP valve 11 selected for this purpose, the threshold CPAP valve opens to vent excess gases, thus keeping airway pressure at just the pressure of the threshold CPAP valve. During expiration, the oxygen containing gas exits the venturi end 13 in a direction substantially toward the vocal folds, aiding mucus transport in that direction. In the embodiment of FIG. 2, the placement of RTC 5 inside TT 9 advantageously requires a single tracheostomy.

Thus, according to the invention, to ensure overall safety of the subject, a thin walled RTC is introduced through a mini-tracheostomy connected to a threshold CPAP or positive end expiratory pressure (PEEP) valve, into the trachea of the subject. The above arrangement provides a means for ensuring that any excess air flow above a predetermined pressure set by the threshold CPAP valve is harmlessly vented after entering the trachea. Optionally, both the RTC and the TT can be combined into one concentric catheter system.

As previously noted, the TGI catheter of the present invention is based on the RTC catheter design disclosed in U.S. Pat. No. 5,186,167, except that the gas defining the venturi is increased from the 0.005 inch to 0.020 inch range in the above patent to approximately 0.025 inch. With the RTC originally designed to rest within an endotracheal tube, which invariably has a small internal diameter compared to the lumen of the trachea, the venturi associated with a standard 0.010 inch gap greatly facilitates expiration particularly at high respiratory rates, and further ensures that mucus is expelled through the endotracheal tube, keeping it clean, with no need for suctioning. However, when the RTC is positioned in the trachea of a human or animal subject (which has an internal diameter much larger than that of the endotracheal tube), as in the case of the present invention, the choice of an optimal gap is guided by the following considerations:

since the trachea is much larger than an endotracheal tube, expiration will not require assist as when it is effected through the endotracheal tube; and the high velocity of gas emerging from the venturi end of the RTC can damage tracheal mucosa, therefore a low gas exit velocity if preferred.

In a study of the spontaneous breathing apparatus according to the invention, where the larger RTC venturi gap is approximately 0.025 inch, no mucosal injury was observed after at least three days. Additionally, mucocilliary transport was observed to have been enhanced by the low velocity gas emerging from the RTC in the cephalad direction (i.e. in the direction of the mouth), which phenomenon additionally facilitates expiration. The trachea was observed to have remained clean of mucus and secretions at least through the duration of the three day studies.

It was further observed that sheep placed on the spontaneous breathing apparatus according to the invention, following instrumentation and recovery from anesthesia, commence glottic breathing within a few hours. Glottic breathing is defined as spontaneous breathing effected by the closing of the glottis, which allows TGI gas flow to fill the lungs to a pressure determined by the threshold CPAP valve. This threshold pressure may, for example, have a value of 5, 10, 15, 20 or even 25 cm $H_2O$, and may be spontaneously sustained for 1, 5, 10 or even 120 seconds, until a spontaneous drive to breathe resumes from a rise in the partial arterial blood level of $CO_2$, which results from prolonged breath holding.

It has been observed that glottic breathing occurs spontaneously in healthy sheep. Glottic breathing may further be facilitated following continuous infusion of a mild tranquilizer such as Diazepam, with glottic breathing commencing within seconds of such infusion. When TGI gas flow is discontinued, it has been observed that a normal breathing pattern resumes within 20 seconds.

With the apparatus and method of the present invention, a great decrease in the effort required for inspiration has been observed, as inferred from pleural pressure changes, as compared to baseline values (that is, to the effort required for inspiration when gas flow to the TGI catheter is stopped). Combined with an advantageous decrease in respiratory rate, it can be estimated that the effort of breathing (referred to as "minute work"), and pressure time product (PTP) associated with breathing, is reduced by an amount in the range from 75% to 95% or more, in healthy sheep.

In preliminary tests administered to sheep with severe acute respiratory failure following oleic acid infusion, glottic breathing has been observed to be the exclusive form of breathing, unlike the case of healthy sheep. Recovery from severe acute respiratory failure with the apparatus and method of the present invention commenced within hours of such pulmonary ventilation, with weaning to room air within 9–12 hours.

EXAMPLE 1

One thin walled catheter having an internal diameter of 4.5 mm was introduced through a mini-tracheostomy. A modified reverse thrust catheter (i.e. one having a venturi gap of approximately 0.025 inch) was passed therethrough. The thin walled catheter was connected to a threshold PEEP valve to ensure that tracheal airway pressure never exceed a desired threshold. The gas being delivered through the RTC was well humidified.

In studies of healthy sheep, upon start of air flow, the respiratory rate decreased from 24–38 per minute to 6–12 per minute, and pleural pressure excursions decreased from 8–12 cm $H_2O$ to 3–5 cm $H_2O$. More importantly, mean airway pressure was 3–6 cm $H_2O$ depending on the threshold PEEP valve, and on air flow. At times, sheep commenced inspiration (with gas delivered through the RTC) with the glottis closed. The above led to a passive filling of lungs, which was limited by the pressure threshold of the threshold PEEP valve. Expiration was initiated when the glottis spontaneously, and briefly, opened. In studies in five sheep, each lasting three days, and at a RTC flow of 10–15 liters per minute, no macroscopic tracheal mucosal injury or accumulation of secretions was found.

EXAMPLE 2

The apparatus and method of the invention were applied in a model of severe oleic acid lung injury in three sheep, mildly sedated with Ketamine, infused with a total dose of 60 mg/kg, in three separate doses 10 minutes apart. Immediately after placing the sheep on this system, their breathing pattern changed, there was prolonged closing of vocal folds during inspiration, with a brief opening of vocal folds during expiration, with all gas to the lungs being delivered through the RTC catheter. The airway plateau pressure equalled that of the threshold PEEP valve. That is, with a threshold PEEP valve having a threshold pressure of 15 cm $H_2O$, the plateau or threshold pressure in the airway was 15 cm $H_2O$ as well. The mean airway pressure of 8–12 cm $H_2O$ was therefore adjustable through choice of the threshold PEEP valve.

The respiratory pattern was in effect similar to Airway Pressure Release Ventilation, although its mechanism is different. The respiratory rate greatly decreased. The pleural pressure excursions decreased, and, combined with decreased respiratory rate, reflected greatly reduced effort of breathing. On improvement in arterial blood gases, Ketamine and $FiO_2$ were progressively reduced. Weaning to room air occurred by 8–12 hours. Chest X-ray films progressively cleared. During the latter part of the study, sheep were allowed to eat and drink ad lib.

The trachea were not suctioned. After weaning to room air, sheep were sacrificed. The trachea was unremarkable, with no accumulation of secretions. The lungs appeared edematous.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A spontaneous breathing apparatus comprising:

a source of oxygen containing gas;

a catheter in flow communication with the source of oxygen containing gas and adapted to be introduced into a subject's trachea through a tracheostomy for delivering oxygen containing gas therein;

a tracheostomy tube disposed adjacent the catheter and having one end adapted to be disposed in the subject's trachea; and a pressure actuated threshold valve connected to another end of the tracheostomy tube, the valve being configured for venting a gas existing within the subject's trachea at the one end of the tracheostomy tube when the gas exceeds a threshold pressure of the valve, the valve thereby being effective for reducing pressure within the subject's trachea when the pressure within the subject's trachea exceeds the threshold pressure, wherein the pressure actuated threshold valve includes a sensor therein for sensing an actuation of the valve to release the gas within the subject's trachea when the pressure within the subject's trachea exceeds the threshold pressure, the spontaneous breathing apparatus further comprising an actuator for one of stopping and reducing a flow of the oxygen containing gas from the source of oxygen containing gas into the catheter when the sensor senses an actuation of the valve.

2. The spontaneous breathing apparatus according to claim 1, wherein the catheter is a reverse thrust catheter comprising a venturi end adapted to direct a flow of the oxygen containing gas in a direction substantially toward the subject's glottis.

3. The spontaneous breathing apparatus according to claim 2, wherein the venturi end comprises:

a catheter tip defining a plurality of holes therein for allowing the oxygen containing gas to exit from the catheter; and a tubular portion connected to the catheter tip for directing the oxygen containing gas emerging from the holes in the direction substantially toward the subject's glottis, the tubular portion and an outer circumference of the catheter together defining a venturi gap therebetween.

4. The spontaneous breathing apparatus according to claim 3, wherein the venturi gap is approximately 0.025 inch.

5. The spontaneous breathing apparatus according to claim 1, wherein the catheter is disposed substantially within the tracheostomy tube thereby forming a catheter-tube assembly, the catheter-tube assembly being adapted to be inserted into the subject's trachea through a single tracheostomy.

6. The spontaneous breathing apparatus according to claim 1, wherein the pressure actuated threshold valve is a threshold continuous positive airway pressure valve.

7. A method comprising the steps of:

providing a source of oxygen containing gas;

placing a catheter in flow communication with the source of oxygen containing gas;

introducing the catheter into a subject's trachea through a tracheostomy for delivering oxygen containing gas therein;

providing a tracheostomy tube disposed adjacent the catheter;

placing one end of the tracheostomy tube in the subject's trachea;

connecting a pressure actuated threshold valve to another end of the tracheostomy tube; and venting, through the valve, a gas existing within the subject's trachea at the one end of the tracheostomy tube when the gas exceeds a threshold pressure of the valve thereby reducing pressure within the subject's trachea when the pressure within the subject's trachea exceeds the threshold pressure.

8. The method according to claim 7, wherein the tracheostomy tube includes a cuff at the one end thereof, the method further comprising the step of preventing the cuff from inflating during a respiratory cycle of the subject.

* * * * *

UNITED STATES PATENT AND TRADEMARK OFFICE
CERTIFICATE OF CORRECTION

PATENT NO.      : 6,655,382 B1
DATED           : December 2, 2003
INVENTOR(S)     : Theodor Kolobow It is certified that error appears in the above-identified patent and that said Letters Patent is hereby corrected as shown below:

<u>Title page,</u>
Item [22], delete "1997" and insert -- 1998 --.

Signed and Sealed this

Fourth Day of May, 2004

JON W. DUDAS
*Acting Director of the United States Patent and Trademark Office*